United States Patent [19]

Suzuki

[11] Patent Number: 5,256,691
[45] Date of Patent: Oct. 26, 1993

[54] OIL-IN-WATER TYPE EMULSIFIED COMPOSITION COMPRISING NON-STEROIDAL ANTIPHLOGISTIC AND ANALGESIC DRUG

[75] Inventor: Takashi Suzuki, Yokohama, Japan

[73] Assignee: Shiseido Company Ltd., Tokyo, Japan

[21] Appl. No.: 768,698

[22] PCT Filed: Mar. 2, 1991

[86] PCT No.: PCT/JP91/00280
§ 371 Date: Oct. 22, 1991
§ 102(e) Date: Oct. 22, 1991

[87] PCT Pub. No.: WO91/12821
PCT Pub. Date: Sep. 5, 1991

[30] Foreign Application Priority Data

Mar. 2, 1990 [JP] Japan .................. 2-49452

[51] Int. Cl.$^5$ ............................. A61K 31/19
[52] U.S. Cl. ................................ 514/510
[58] Field of Search ................. 514/567, 570

[56] References Cited

U.S. PATENT DOCUMENTS 4,465,629 8/1984 Maughan .................. 424/195

FOREIGN PATENT DOCUMENTS

| 0216303 | 4/1987 | European Pat. Off. . |
| 0245756 | 11/1987 | European Pat. Off. . |
| 0055029 | 6/1992 | European Pat. Off. . |
| 2633516 | 5/1990 | France . |
| 53-113787 | 10/1978 | Japan . |
| 54-052734 | 4/1979 | Japan . |
| 58-185514 | 10/1983 | Japan . |
| 59-033211 | 2/1984 | Japan . |
| 59-088419 | 5/1984 | Japan . |
| 59-116212 | 7/1984 | Japan . |
| 60-008215 | 1/1985 | Japan . |
| 61-215320 | 9/1986 | Japan . |
| 63-150221 | 6/1988 | Japan . |
| 64-013020 | 1/1989 | Japan . |
| 1-242521 | 9/1989 | Japan . |

OTHER PUBLICATIONS

Chem. Abst. 105-102614G (1986).

Primary Examiner—S. J. Friedman
Attorney, Agent, or Firm—Wegner, Cantor, Mueller & Player

[57] ABSTRACT

A stable oil-in-water type emulsified composition, which comprises a stable non-steroidal antiphlogistic and analgesic drug by using a combination of a monoalkylglyceryl ether, particularly an ether compound having a $C_{12-22}$ alkyl group in the alkyl moiety and a hydrophilic surface-active agent.

In particular, when the drug is in the form of salts, the stability of the composition can be increased thereof by adding an ion consisting of $HSO_3-$, $SO_3--$ or $S_2O_5--$.

4 Claims, No Drawings

OIL-IN-WATER TYPE EMULSIFIED COMPOSITION COMPRISING NON-STEROIDAL ANTIPHLOGISTIC AND ANALGESIC DRUG

TECHNICAL FIELD

The present invention relates to a novel oil-in-water type (hereinafter may be referred to "o/w type") emulsified composition comprising a non-steroidal antiphlogistic and analgesic drug. Specifically, the composition in accordance with the present invention contains a monoalkylglyceryl ether and hydrophilic surface-active agent, and thus the composition is to be stabilized and useful for a pharmaceutical preparation for external use.

BACKGROUND ART

In general, it is feared that a non-steroidal antiphlogistic and analgesic drugs (or anti-inflammatories) cause side effects when they are administrated orally or rectally. For the purpose of solving the side effects, a wide variety of pharmaceutical preparations for external use which are administrated directly in topical portions have been developed. In many such pharmaceutical preparations, since most non-steroidal antiphlogistic and analgesic drugs do not easily dissolve in both water and oil, lower alcohols, polyvalent alcohols, fatty acid esters, crotamiton, surfactants, or the like are combined to dissolve the drugs or the medicine is dispersed in a medium in micro-powder form such as crystal, and then water-soluble polymeric compounds are formulated in order to ensure the stabilization of the dispersion. Even the salt compounds of the non-steroidal antiphlogistic and analgesic drugs in the form of sodium salts are only slightly soluble in water, and thus attempts to use various methods have been made for preparation.

With examples of the method, since skin safety is generally lowered when a lower alcohol or a polyhydric alcohol such as propylene glycol is formulated in a large amount for the purpose of dissolving the medicine, an aqueous emulsified preparation not using any lower alcohol has been proposed (see, for example, Japanese Unexamined Patent Publications (Kokai) No. 57-98209, No. 58-185514, No. 59-116212 and No. 61-215320). In almost all of these inventions, the dispersion is thickened with a water-soluble polymeric compound, and thus it is very difficult to enhance their thermodynamic activities in terms of the separation of the medicine with the passage of time and the discharge of the medicine. Further, because of stickiness due to a large amount of the water-soluble polymeric compound being formulated, it is not preferred from the viewpoint of its texture. On the other hand, for the purpose of enhancing the discharge of the medicine from the base, an invention in which the medicine is prepared in the saturated state (see Japanese Unexamined Patent Publication (Kokai) No. 63-150221) has been disclosed. Due to the formulation of a higher alcohol, the invention, however, has the problem that the esterification reaction with the medicine causes a significant impairment in the compound's stability. In particular, in the case where the medicine has a low stable pH region, it is apt to bring about the esterification with the higher alcohol, the reaction being increasingly likely to occur when the water formulation is larger. On the other hand, since there is poor solubility in water even when the non-steroid agent is a salt (or a compound in the form of the salt), the invention in which the preparation is made into an oleaginous ointment has been known (see Japanese Unexamined Patent Publication (Kokai) No. 59-33211). The agent thus prepared is unduly greasy and tends to stain clothes; thus, it is not necessarily preferred. Furthermore, Inventions of a cream preparation (see Japanese Unexamined Patent Publication (Kokai) No. 64-13020) and a solution preparation (see Japanese Unexamined Patent Publication (Kokai) No. 1-242521) have been disclosed.

However, in preparation of the cream, the water-soluble polymeric compound or a higher alcohol is used, and thus preparations using the compounds as described above are associated with common problems.

Also, to provide a cream or ointment, it is known that a pharmaceutical preparation for external use contains a combination of α-monoglyceryl ether and an oily substance in the form of paste as well as a biological active substance of percutaneous absorption (see Japanese Examined Patent Publication (Kokoku) 2-44815), and that an oil-in-water type emulsifying stabilizer consists of N-long chain acyl acidic amino acids and glycerol monoalkyl ethers. The former increases the percutaneous absorption by increasing occlusion. Accordingly, the publication discloses mainly preparations belonging to water-in-oil (w/o) as a type of emulsifying agent. Although this preparation is improved to some degree, the preparation is greasy. Further, the preparation is only used as a lipophilic surface-active agent, and thus it is very difficult to emulsify the same because the surface-active agent is dissolved in a higher polar oil ingredient when the oil is used in a large amount to dissolve the medicine. Accordingly, it is difficult for a medicine in the form of a salt, such as diclofenac sodium, to be stable at a high concentration. Although the latter is in a stable state to the emulsified composition itself, the emulsifying stabilizer, is not sufficiently effective as can be seen from the components thereof when the stabilizer is applied to a medicine which may be unstabilized in acidic condition.

Although the aforementioned emulsified compositions and pharmaceutical preparations independently solve certain problems, they are not entirely satisfactory in application or stability.

Accordingly, the object of the present invention is to provide a useful pharmaceutical preparation for external use with an emulsified composition which has excellent texture and belongs to a o/w type, and comprises a non-steroidal antiphlogistic and analgesic drug.

DISCLOSURE OF INVENTION

For accomplishing the above object, the present inventors have found that an emulsified composition comprising a combination of a monoalkylglyceryl ether and a hydrophilic surface-active agent can provide a stable emulsified composition containing a non-steroidal antiphlogistic and analgesic drug, and further, in particular, maintains the medicine itself is stable.

Namely, the above problems are solved by an oil-in-water type emulsified composition containing a non-steroidal antiphlogistic and analgesic drug; wherein said composition comprises a monoalkylglyceryl ether and a hydrophilic surface-active agent.

BEST MODE FOR CARRYING OUT THE INVENTION

The non-steroidal antiphlogistic and analgesic drugs contained in the composition of the invention are not restricted to any specific type as long as they satisfy the object of the present invention, but include specifically compounds having a carboxyl group on a molecule thereof. More specifically, they can include indomethacin, flurbiprofen, ibuprofen, flufenamic acid, mefenamic acid, diclofenac, ketoprofen, tolfenamic acid, and tianoprofenic acid. In particular, as compounds in the form of salts of the non-steroidal drugs, alkaline metal salts (e.g. sodium and potassium salts) derived from diclofenac, tolmetin, anfenac, flufenamic acid, fenoprofen, meclomen, and roxoprofen, are preferably included.

The content of the non-steroidal antiphlogistic and analgesic drug or salt thereof in the preparation of the present invention is not restricted because the optimum amount varies depending upon the form of drug and the kind of the drug to be used, but may be in an amount that can express the medicinal effects, which is generally 0.1 to 10% by weight, preferably 0.5 to 5.0% by weight.

The monoalkylglyceryl ethers which are an essential ingredient of the present invention, are those generally known which hydrate with water to act as a solidifying agent (creaming agents) similar to higher alcohols used in the technical field of cream preparation such as cosmetics. Surprisingly, the application of such ethers to the non-steroidal antiphlogistic and analgesic drug not only markedly stabilizes cream preparation but also the preparation of the gel and lotion types. As effective monoalkylglyceryl ethers, but not limited to, the linear chain ethers whose alkyl group has 12 to 22 carbon atoms can be included. Consequently, the alkyl groups possessing these ethers include the lauryl group, myristyl group, palmityl group, stearyl group, arachidol group, and behenyl group. If the length of the alkyl groups of these ethers is unduly short, there is insufficient solidifying effect, and conversely, if it is unduly long, hydrophobicity is increased thereby weakening the hydration to water and reducing the solidifying effect; this is not preferred. Furthermore, since α-monoglyceryl ethers bearing a branched chain and a unsaturated bond, as disclosed in Japanese Examined Patent Publication (Kokoku) No. 2-44815 aforesaid, have no solidifying effect, the ethers are not preferred for the preparations of the present invention. Consequently, as the ethers which are particularly preferred in the present invention, hexadecyl glyceryl ether (chimyl alcohol) and octadecyl glyceryl ether (batyl alcohol) each having a parmytyl group or stearyl group which has 16 or 18 carbon atoms respectively can be included. These monoalkylglyceryl ethers can be used alone or as optional mixtures. They are generally formulated in the preparation in a ratio of 0.5 to 10% by weight, preferably 1.0 to 5 0% by weight.

Another essential ingredient of the present invention, is hydrophilic surface-active agent classified as a o/w type in the present preparations. For such surface-active agents any type of non-ionic surface active agents and ionic surface active agents may be used. Useful non-ionic surface active agents are included, for example, polyoxyethylene sorbitan fatty esters, polyethylene glycol fatty esters, polyoxyethylene glycerol fatty esters, polyethylene alkylethers, polyoxyethylene-polyoxypropylene alkylethers, polyoxyethylene alkylphenyl ethers, polyoxyethylene hydrogenated castor oil, poly-glycerol fatty esters, sugar esters, and the like. Further, useful ionic surface active agents, for example, alkyl sulfates, polyoxyethylene alkylether sulfates, alkylphosphates, alkylsulfon-carboxylates, triethanolamine, diethanolamine, di-isopropanolamine, and basic amino acid (e.g., lysine, arginine) are also included. In particular, non-ionic surface active agents are preferred in that the agents have a high stability for various medicine. Such surface-active agents are generally formulated in the preparation in a range from 0.05 to 20% by weight, and preferably in a range from 0.1 to 10% by weight.

In accordance with the present invention, although any non-steroidal antiphlogistic and analgesic drugs described above can form a stable emulsified composition, it is preferable that sulfur containing compounds that generate at least one member of ion selected from groups consisting of $HSO_3-$, $SO_3-$ and $S_2O_5--$, are further incorporated into the preparation, and the stability of the same can be increased when the medicine is applied in the form of a salt as described above. The emulsified composition of the invention is significantly prevented from yellowing by the addition of said compounds to the preparation, for external use. Examples of the sulfur containing compounds are included hydrogensulfites (alkali metal hydrogensulfites such as sodium hydrogensulfite, potassium hydrogensulfite; ammonium hydrogensulfite), sulfites (alkali metal sulfites such as sodium sulfite and potassium sulfite; alkaline earth metal sulfites such as calcium sulfite and barium sulfite), pyrosulfites (alkali metal pyrosulfites such as sodium pyrosulfite and potassium pyrosulfite). The amounts of these compounds to be formulated which depend upon the pH of the system, are 0.02 to 0.5% by weight, preferably 0.05 to 0.2% by weight, based on the preparation. Amounts exceeding 0.5% by weight are not preferable because the emulsification becomes difficult.

Optionally, solid oils which are usually used in various preparations for external use such as solid oils such as beeswax, stearic acid, and hydrogenated hardened oil; semi-solid oils such as vaseline, lanoline, tallow, lard and hardened oil; liquid paraffin; squalane; silicone; plant oils such as olive oil and sesame oil; humectants such as propylene glycol, glycerine, polyglycerine and 1,3-butylene glycol; lower alcohols; water-soluble polymeric materials such as bentonite and carboxyvinyl polymer; thickening agents such as lecithin; antiseptics; buffering agents; and anti-oxidant may be added corresponding to the shape of the drug.

The preparation of the non-steroidal antiphlogistic and analgesic integument agent of the present invention can be carried out by various preparation methods already known in the art. For example, the medicine is heated to 50-60° C. and dissolved in a polar oil such as crotamiton and sebacic acid diesters. Subsequently, stearic acid, batyl alcohol, a hardened oil, a light liquid paraffin and a surfactant are heated to 75-80° C. and dissolved, and after the temperature is controlled to 70° C., the medical substrate layer prepared in advance is added to provide an oil phase.

On the other hand, to purified water are added glycerine, 1,3-butylene glycol, buffers, sodium hydroxide, carboxyvinyl polymer and sodium sulfite, and the mixture is heated to 70° C., stirred and dissolved to make a water phase. While stirring, the oil phase is gradually added to the water phase, and a preemulsification is carried out, after which the mixture is treated with a homomixer, and then stirred and cooled thereby obtaining a stable o/w type cream.

Further, when it is desired to enhance the thermodynamic flowability of the medicine in the base, a stable preparation excelling in percutaneous absorption can be made by using a two-stage emulsion method (see Japanese Unexamined Patent Publication (Kokai) No. 63-150221) utilizing the monoalkylglyceryl ether in place of a higher alcohol.

EXAMPLES

The following examples illustrate the invention but should be interpreted as limitations thereon.

EXAMPLE 1

| | Cream Preparation | |
|---|---|---|
| Composition | The Invention 1 | Comp. Example 1 |
| Indomethacin | 1.0% | 1.0% |
| Crotamiton | 2.0 | 2.0 |
| Panaceito 875 (supplied from Nippon Yushi Co., Ltd) | 15.0 | 10.0 |
| Light liquid paraffin | 4.0 | 2.0 |
| Stearic acid | 4.5 | 2.0 |
| Hydrogenated castor oil | 5.0 | 5.0 |
| POE (40 mole) Stearic acid ester | 2.0 | 2.0 |
| Glycerine monostearate | 3.0 | 3.0 |
| Cetanol | — | 6.0 |
| Batyl alcohol | 1.7 | — |
| Etylparaben | 0.2 | 0.2 |
| Glycerine | 10.0 | 10.0 |
| Sorbitol | 5.0 | 5.0 |
| Sodium sulfite | 0.1 | 0.1 |
| Purified water | controlled to 100% | |
| | (pH = 4.80) | (pH = 4.86) |

PREPARATION AND STABILITY TESTS

Method for Preparation of Indomethacin Cream 1.0% of indomethacin was added to 2.0% of crotamiton and 15% of Panaceito 875, and thermally dissolved at 60–70° C. Separately, 4% of light liquid paraffin, 4.5% of stearic acid, 5% of hydrogenated castor oil, 1.6% of batyl alcohol, 5% of surfactant and 0.2% of ethylparaben were heated to 70–80%, stirred and dissolved, after which the indomethacin phase having been dissolved in advance was added and the temperature controlled to 70±2° C. to prepare an oil phase. On the other hand, 10% of glycerine, 5.0% of sorbitol and 0.1% of sodium sulfite were added to purified water, thermally dissolved, and the temperature controlled to 70±2° C. While stirring, the oil phase was gradually added to the water phase, the preemulsification and a homomixer treatment were carried out, after which the mixture was stirred and cooled to obtain a cream.

Quantitative Determination of Indomethacin 0.5 g of the preparation was weighed and 5 ml of valerophenone as an inner standard and methanol were added to prepare a sample. Using acetonitrile + water (55:45) as a mobile phase, indomethacin was quantitatively determined by HPLC with Column Capsule Pack $C_{18}$. The results are shown in Table 1.

TABLE 1

| | 50° C., 2 Months | 0° C., 2 Months |
|---|---|---|
| The Invention 1 | 93.90% | 99.90% |
| Comp. Example 1 | 50.92% | 99.80% |

EXAMPLE 2

| Gel Preparation | |
|---|---|
| Composition | |
| Sodium diclofenac | 2.0% |
| Isostearic acid | 5.0 |
| Diethyl sebacate | 15.0 |
| Crotamiton | 2.5 |
| Ethylparaben | 0.2 |
| Batyl alcohol | 0.5 |
| Glycerine monostearate | 1.0 |
| Light liquid paraffin | 2.0 |
| POE (60 mole) hydrogenated castor oil derivative | 1.5 |
| Glycerine | 5.0 |
| Hibiswako-104 (carboxyvinyl plymer) | 0.2 |
| Diisopropanolamine | 0.2 |
| Stabilizer | *0.02–0.2 |
| Purified water | controlled to 100% (pH = 7.26) |
| *Stabilizer | |
| BHT | 0.02 |
| dl-α-tocopherol | 0.05 |
| Sodium sulfite | 0.2 |
| Sodiumhydrogen sulfite | 0.2 |
| Sodium pyrosulfite | 0.1 |

2.0 g of sodium diclofenac was added to the mixture of isostearic acid, diethyl sebacate, crotamiton, ethylparaben and light liquid paraffin having the aforementioned composition, and thermally dissolved at 70–75° C., after which the mixture was allowed to cool to room temperature to prepare an oil phase. On the other hand, POE (60 mole) hydrogenated castor oil derivative was added to glycerine in the ratio described above and thermally dissolved, after which a part of purified water was added and emulsified. Subsequently, it was treated by means of a homomixer at 12000 rpm for 3 minutes to prepare an emulsion base. On the other hand, Hibiswako 104 (trade name: carboxyvinyl polymer) was dissolved in a part of purified water and then diisopropanolamine was added for the neutralization, after which a pre-pared emulsion base was added and thoroughly stirred until the mixture became uniform. Finally, the solution in which a stabilizer had been completely dissolved in a part of purified water was added to obtain a gel preparation. (The stabilizer in the oil-soluble phase, BHT and tocopherol (Comparative Example) were added to the oil phase.)

After 25 g of these gelled ointments were charged in alumina tubes, they were stored at 50° C., room temperature, 40° C., and 0° C for 2 months, and color changes were observed. The results are shown in the following Table 2.

TABLE 2

| | | 0° C. | Room Temp. | 50° C. | 40° C. |
|---|---|---|---|---|---|
| Comp. Ex | BHT | o | o | xx | x |
| | α-tocopherol | o | o | xx | x |
| the invention | Sodium sulfite | o | o | o | o |
| | Sodium-hydrogen sulfite | o | o | o | o |
| | Sodium pyrosulfite | c | c | c | c | xx significant discoloration is observed
x discoloration is observed
o discoloration is not observed
Δ a slight discoloration is observed

EXAMPLE 3

Cream Preparation 3.0 g of sodium diclofenac was thermally dissolved in 8 g of isostearic acid, 20 g of diethyl sebacate, 2.0 g of crotamiton 25 g of octyldecyloctyltriglyceride (ODO), 3 g of squalane, 5 g of hydrogenated castor oil, 2 g of batyl alcohol and 0.2 g of ethylparaben, and the temperature was controlled to 50° C. to prepare an oil phase. On the other hand, 3.5 g of POE (60 mole) hydrogenated castor oil derivative was thermally dissolved in 8 g of glycerine and 7 g of propylene glycol, a part of purified water was added and the temperature was controlled to 50° C. to prepare a water phase. The previously prepared oil phase was gradually added by using Adihomomixer (supplied from Tokusyu Kako Co., Ltd.) to carry out the emulsification. 0.1 g of sodium sulfite which had been dissolved in a part of purified water and the remaining purified water was added to obtain the total weight of 100 g to obtain sodium diclofenac creams. These creams were charged in metal tubes and were stored at 50° C. for 2 months, no discoloration change was observed in any case.

EXAMPLE 4

Cream Preparation 2.0 g of sodium diclofenac, 4.0 g of oleic acid, 2.0 g of crotamiton, 13.0 g of diisopropyladipate, 6.0 g of squalane and the balance of anti-oxidant were mixed, and the mixture was thermally dissolved at a temperature controlled to 50°±2° C. to prepare an oil phase. To 25 g of purified water was added 1.0 g of POE (45 mole) stearyl ether 0.5 g of decaglycerine mono oleate and 5.0 g of glycerine, the mixture was heated at 40° C. and the previously prepared oil phase was added to emulsify, and thereby concentrated emulsion was obtained. On the other hand, 5.0 g of stearic acid, 4.0 g of hydrogenated castor oil, 2.0 g of batyl alcohol, 3.0 g of light liquid paraffin, 1.0 g of POE (45 mole) stearyl ether, 5.0 g of glycerine mono stearate and 0.1 g of ethylparaben were thermally dissolved, and the temperature was controlled to prepare an oil phase. While stirring at 70° C., the oil phase was gradually added to the water phase mixed with 0.1 g of sodium sulfite and 0.2 g of sodium hydroxide, the mixture was treated by means of a homomixer and the previously prepared coacervation was added; the resulting mixture was also treated by means of a homomixer, and was cooled to obtain a stable o/w type cream.

INDUSTRIAL APPLICATION

In accordance with the present invention, a stable oil-in-water (o/w) type emulsified composition comprising a non-steroidal antiphlogistic and analgesic drug is useful for pharmaceutical preparation for external use.

Such stability is accomplished by using a monoalkylglyceryl ether and hydrophilic surface-active agent so as to emulsify the medicine.

I claim:

1. An oil-in-water type emulsified composition containing a diclofenac salt, wherein the composition comprises a stabilizing-effective amount of a monoalkylglyceryl ether and hydrophilic surface-active agent.

2. The composition according to claim 1, wherein the monoalkylglyceryl ether has an alkyl group containing 12-22 carbon atoms in the alkyl moiety.

3. The composition according to claim 2, wherein the monoalkylglyceryl ether is chimyl alcohol or batyl alcohol.

4. The composition according to claim 1, wherein the composition further contains a sulfur containing compound that generates at least one member of an ion selected from groups consisting of $HSO_3-$, $SO_3--$ and $S_2O_5--$.

* * * * *